United States Patent
Polikarpus et al.

(10) Patent No.: US 7,138,604 B2
(45) Date of Patent: Nov. 21, 2006

(54) CERAMIC DEVICE, SENSOR DEVICE, METHOD OF MAKING THE SAME, AND METHOD FOR SENSING GAS

(75) Inventors: Kaius K. Polikarpus, Grand Blanc, MI (US); Walter T. Symons, Grand Blanc, MI (US); Charles Scott Nelson, Clio, MI (US); Rick D. Kerr, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 228 days.

(21) Appl. No.: 10/820,085

(22) Filed: Apr. 6, 2004

(65) Prior Publication Data

US 2004/0217098 A1    Nov. 4, 2004

Related U.S. Application Data

(60) Provisional application No. 60/467,415, filed on May 2, 2003.

(51) Int. Cl.
*H05B 1/02*    (2006.01)

(52) U.S. Cl. .................. 219/209; 219/505; 219/538; 219/541

(58) Field of Classification Search ............. 219/504, 219/505, 202, 209, 205, 457, 538, 541
See application file for complete search history.

(56) References Cited

U.S. PATENT DOCUMENTS

| | | | | |
|---|---|---|---|---|
| 5,344,545 A | * | 9/1994 | Tsukada et al. | 204/415 |
| 5,490,412 A | * | 2/1996 | Duce et al. | 73/23.31 |
| 2003/0159928 A1 | * | 8/2003 | Kojima et al. | 204/408 |
| 2005/0101161 A1 | * | 5/2005 | Weiblen et al. | 439/37 |

* cited by examiner

*Primary Examiner*—Mark Paschall
(74) *Attorney, Agent, or Firm*—Jimmy L. Funke (57) ABSTRACT

A sensor may comprise a first electrode and a second electrode in mutual ionic communication with an electrolyte, a first socket disposed near a rear portion of a sensor element, a first lead disposed in electrical communication with the first electrode and in physical contact with the first socket and configured for electrical communication with a first terminal element, a second socket disposed near the rear portion of the sensor element, and a second lead disposed in electrical communication with the second electrode and in physical contact with the second socket and configured for electrical communication with a second terminal element. The first socket is disposed through at least one of an edge and an end of the sensor element, and the second socket is disposed through at least one of the edge and the end of the sensor element.

18 Claims, 2 Drawing Sheets

CERAMIC DEVICE, SENSOR DEVICE, METHOD OF MAKING THE SAME, AND METHOD FOR SENSING GAS

CROSS-REFERENCE TO RELATED APPLICATION

The present application claims priority to Provisional U.S. Patent Application No. 60/467,415 filed May 2, 2003, which is hereby incorporated by reference in its entirety.

BACKGROUND

Sensors, in particular gas sensors, have been utilized for many years in several industries (e.g., in furnaces and other enclosures, in exhaust streams such as flues, exhaust conduits, and the like, and in other areas). For example, the automotive industry has used exhaust gas sensors in automotive vehicles to sense the composition of exhaust gases, for example, oxygen. A sensor is used to determine the exhaust gas content for alteration and optimization of the air to fuel ratio for combustion.

One type of sensor uses an ionically conductive solid electrolyte between porous electrodes. For oxygen detection, solid electrolyte sensors are used to measure oxygen activity differences between an unknown gas sample and a known gas sample. In the use of a sensor for automotive exhaust, the unknown gas is exhaust and the known gas, i.e., reference gas, is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle may consist of an ionically conductive solid electrolyte material disposed between a porous electrode with a porous protective overcoat exposed to exhaust gases ("sensing electrode"), and a porous electrode exposed to the partial pressure of a known gas "reference electrode". Sensors used in automotive applications may use a yttria stabilized zirconia electrolyte with porous platinum electrodes, operating in potentiometric mode, to detect the relative amounts of a particular gas, such as oxygen for example, that is present in an automobile engine's exhaust. Also, a sensor may have a ceramic heater attached to help maintain the sensor's ionic conductivity at low exhaust temperatures. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating in fuel-rich or fuel-lean conditions, without quantifying the actual air-to-fuel ratio of the exhaust mixture.

In planar sensors, leads embedded in the sensor element may be used to electrically communicate with the electrodes and/or heater. A wire that is external to the sensor element may be in electrical communication with the leads through the use of via-holes. These via-holes are filled with a precious metal paste that when fired connects the leads to contact pads located on the external surface of the sensor element. In a subsequent step, a connector joined to the wire may be connected to the contact pads. As sensor elements employ more leads, however, this interconnection becomes increasingly complex. Moreover, additional leads relate to the use of more via-holes, which further relate to the use of more precious metal used to fill additional via-holes and make the associated contact pads.

There thus remains a need for sensor elements having an improved electrical interconnection.

SUMMARY

Disclosed herein are sensors, ceramic devices, methods for making sensor devices, and methods for sensing gas. In one embodiment, the sensor comprises: a first electrode and a second electrode in mutual ionic communication with an electrolyte; a first socket defining a first chamber configured to receive a first terminal element; a first lead disposed in electrical communication with the first electrode and in physical contact with the first socket and configured for electrical communication with the first terminal element; a second socket defining a second chamber configured to receive a second terminal element; and a second lead disposed in electrical communication with the second electrode and in physical contact with the second socket and configured for electrical communication with the second terminal element.

In another embodiment, the sensor comprises: a wiring harness and a sensor element. The wiring harness is configured for electrical communication with a control module and comprises a first terminal element in electrical communication with a first wire, a second terminal element in electrical communication with a second wire, first heater terminal element in electrical communication with a first heater wire, and second heater terminal element in electrical communication with a second heater wire. The sensor element, which has a rear portion disposed at an end of the sensor element opposite a first electrode, comprises the first electrode and a second electrode in mutual ionic communication with an electrolyte; a heater element in thermal communication with the first electrode and the second electrode; a first socket defining a first chamber configured to receive the first terminal element; a first lead disposed in electrical communication with the first electrode and in physical contact with the first socket; a second socket defining a second chamber configured to receive the second terminal element; a second lead disposed in electrical communication with the second electrode and in physical contact with the second socket; a first heater socket defining a first heater chamber configured to receive the first heater terminal element; a first heater lead disposed in electrical communication with the heater element in physical contact with the first heater socket; a second heater socket defining a second chamber configured to receive the second heater terminal element; and a second heater lead disposed in electrical communication with the heater element in physical contact with the second heater socket. The first terminal element is in electrical communication with the first lead, the second terminal element is in electrical communication with the second lead, the first heater terminal element is in electrical communication with the first heater lead, and the second heater terminal element is in electrical communication with the second heater lead.

In yet another embodiment, the sensor comprises: a wiring harness and a sensor element. The wiring harness is configured for electrical communication with a control module and comprises a first terminal element in physical contact and electrical communication with a first wire, and a second terminal element in physical contact and electrical communication with a second wire. The sensor element has a rear portion disposed at an end opposite the first electrode, and comprises a first electrode and a second electrode in mutual ionic communication with an electrolyte, a first socket disposed near the rear portion of the sensor element, a first lead disposed in electrical communication with the first electrode and in physical contact with the first socket, a second socket disposed near the rear portion of the sensor element, a second lead disposed in electrical communication with the second electrode and in physical contact with the second socket. The first terminal element is in physical contact with the first lead, and the second terminal element is in physical contact with the second lead.

In one embodiment, a method for making a sensor, comprises forming a sensing element comprising a first electrode and a second electrode on an electrolyte layer, with a first lead disposed from the first electrode to a rear portion of the first element and a second lead from the second electrode to the rear portion; forming a first socket, wherein the first lead extends into the first socket; forming a second socket, wherein the second lead extends into the second socket; and firing the sensor element such that the first socket defines a first chamber configured to receive a first terminal element and the second socket defines a second chamber configured to receive a second terminal element.

In one embodiment, a method for sensing a gas, comprises contacting a sensor element with a gas to be sensed and producing an electromotive force. The sensor element comprises a first electrode and a second electrode in mutual ionic communication with an electrolyte, a first socket defining a first chamber configured to receive a first terminal element, the first terminal element disposed in the first socket and in physical and electrical communication with a first wire, a first lead disposed in electrical communication with the first electrode and in physical and electrical communication with the first terminal element, a second socket defining a second chamber configured to receive a second terminal element, the second terminal element disposed in the second socket and in physical and electrical communication with a second wire, and a second lead disposed in electrical communication with the second electrode and in physical and electrical communication with the second terminal element. The first terminal element and the second terminal element are in electrical communication with a control module.

In one embodiment, the ceramic device comprises: a first lead and a second lead disposed within a ceramic element, a first socket disposed near a rear portion of the ceramic element and defining a first chamber for receiving a first terminal element; a second socket disposed near a rear portion of the ceramic element and defining a second chamber for receiving a second terminal element; a first resistor lead and a second resistor lead are disposed on a resistor plane within the ceramic element; a first resistor socket disposed in a rear portion of the ceramic element and defining a first resistor chamber for receiving a first resistor terminal element, and a second resistor socket disposed in a rear portion of the ceramic element and defining a second resistor chamber for receiving a second resistor terminal element wherein the second resistor lead is disposed in physical communication with and extends into the second resistor socket; a first resistor terminal element disposed in the first resistor socket and in electrical communication with the first resistor lead, and a second resistor terminal element disposed in the second resistor socket and in electrical communication with the second resistor lead. The first lead is disposed in physical communication with and extends into the first socket, and the first socket is disposed on a first socket plane that is parallel a first lead plane comprising the first lead. The first terminal element is disposed in the first socket and in electrical communication with the first lead. The second lead is disposed in physical communication with and extends into the second socket, and the second socket is disposed on a second socket plane that is parallel a second lead plane comprising the second lead. The second terminal element disposed in the second socket and in electrical communication with the second lead. The first resistor lead is disposed in physical communication with and extends into the first resistor socket. The first resistor socket and the second resistor socket are disposed on a resistor socket plane that is parallel to the resistor plane.

The above described and other features are exemplified by the following figures and detailed description.

DRAWINGS

Referring now to the figures, which are exemplary embodiments, and wherein the like elements are numbered alike.

DETAILED DESCRIPTION

Although described in connection with an oxygen sensor, it is to be understood that the sensor could be a nitrogen oxide sensor, hydrogen sensor, hydrocarbon sensor, ammonia sensor, or the like. Furthermore, while oxygen is the reference gas used in the description disclosed herein, it should be understood that other gases could be employed as reference gases. Additionally, ceramic devices other than electrochemical sensors may employ the described interconnection method, some such devices include the planar gas sensor, field effect transistor (FET), semiconductor, metal oxide (resistive), or resistance temperature detectors (RTD), low/high temperature co-fired ceramic circuit applications (LTCC and HTCC, respectively), and the like. Also, although a planar element is described and illustrated in the figures, the electrical connection technique (socket location, design, use of terminal elements, and leads disposed into the sockets) can also be employed with a round element (e.g., instead of employing planar layers, the layers would be wrapped, rolled, or the like, around a mandrel, tube, rod, or the like. Additionally, it is noted that greater than one electrochemical cell can be employed.

It should further be noted that the terms "first," "second," and the like herein do not denote any order quantity, or importance, but rather are used to distinguish one element from another, and the terms "a" and "an" herein do not denote a limitation of quantity, but rather denote the presence of at least one of the referenced item. Furthermore, all ranges disclosed herein are inclusive and combinable (e.g., ranges of "up to about 25 wt. %, with about 5 wt. % to about 20 wt. % desired, and about 10 wt. % to about 15 wt. % more desired," is inclusive of the endpoints and all intermediate values of the ranges, e.g., "about 5 wt. % to about 25 wt. %, about 5 wt. % to about 15 wt. %" etc.).

Figure 1:
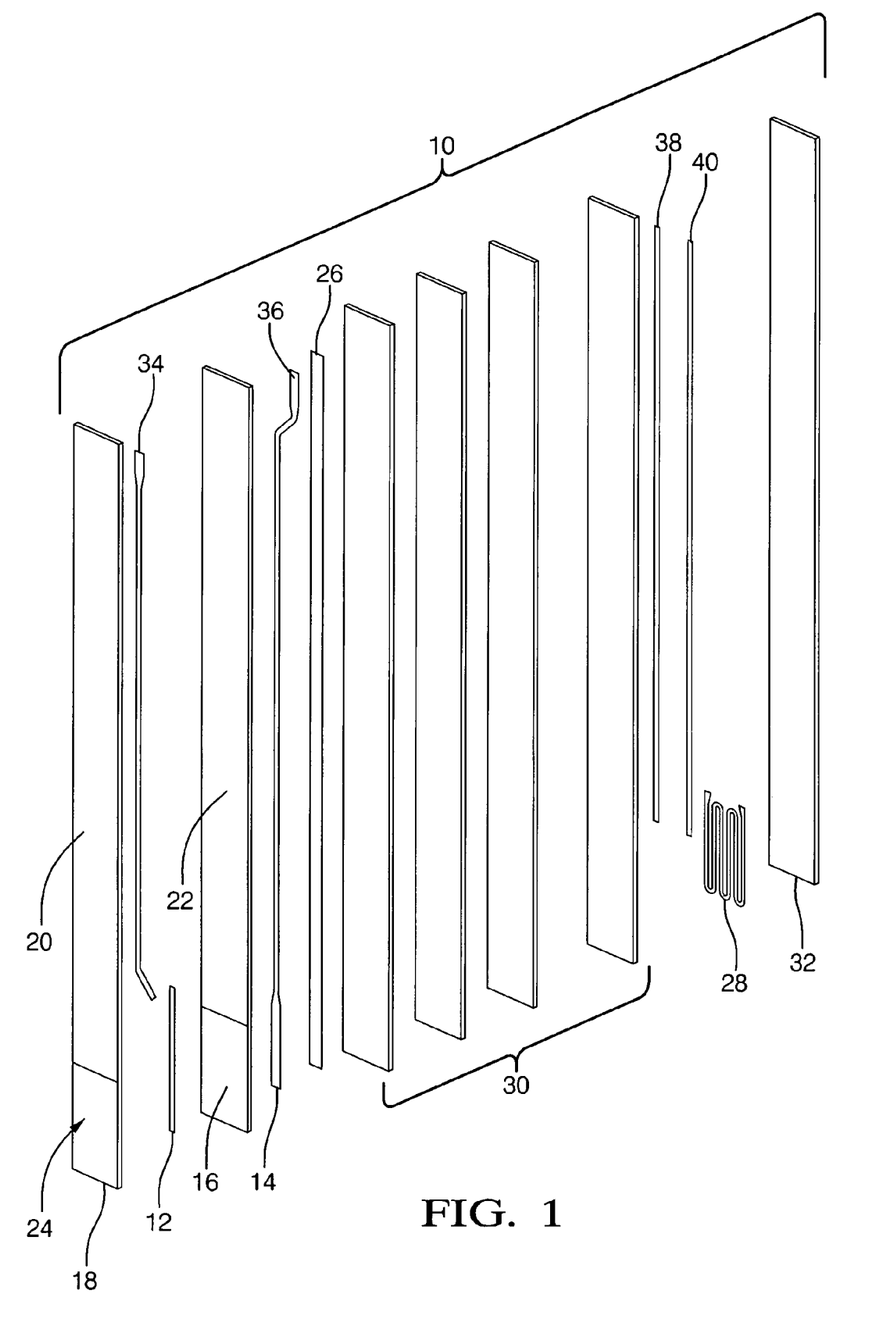
FIG. 1 is an expanded isometric view of an exemplary embodiment of a gas sensor element.

Referring to FIG. 1, an exemplary planar gas sensor element 10 is illustrated. The sensing (i.e., first, exhaust gas, or outer) electrode 12 and the reference gas (i.e., second or inner) electrode 14 are disposed on opposite sides of, and adjacent to, an electrolyte 16 creating an electrochemical cell (12/16/14). The electrolyte 16 may be disposed adjacent to or as an insert within a dielectric substrate layer 22. On the side of the sensing electrode 12, opposite solid electrolyte 16, is a protective layer 18 that enables fluid communication between the sensing electrode 12 and the gas to be sensed (e.g., exhaust gas). This protective layer 18 may be disposed adjacent to or as an insert within a substrate layer 20, or may form the entire layer. Disposed over at least a portion of the protective layer 18, adjacent the sensing electrode 12 is a protective coating 24.

Meanwhile, disposed on the side of the reference electrode 14, opposite solid electrolyte 16, may be an optional reference gas channel 26, which is in fluid communication with the reference electrode 14 and optionally with the ambient atmosphere and/or the exhaust gas. Disposed on a side of the reference gas channel 26, opposite the reference electrode 14 may optionally be a resistor (e.g., a heater element) 28 for maintaining sensor element 10 at a desired operating temperature. Disposed between the reference gas channel 26 and the heater element 28, as well as on a side of the heater opposite the reference gas channel 26, can be one or more insulating layers 30, 32.

Figure 2:
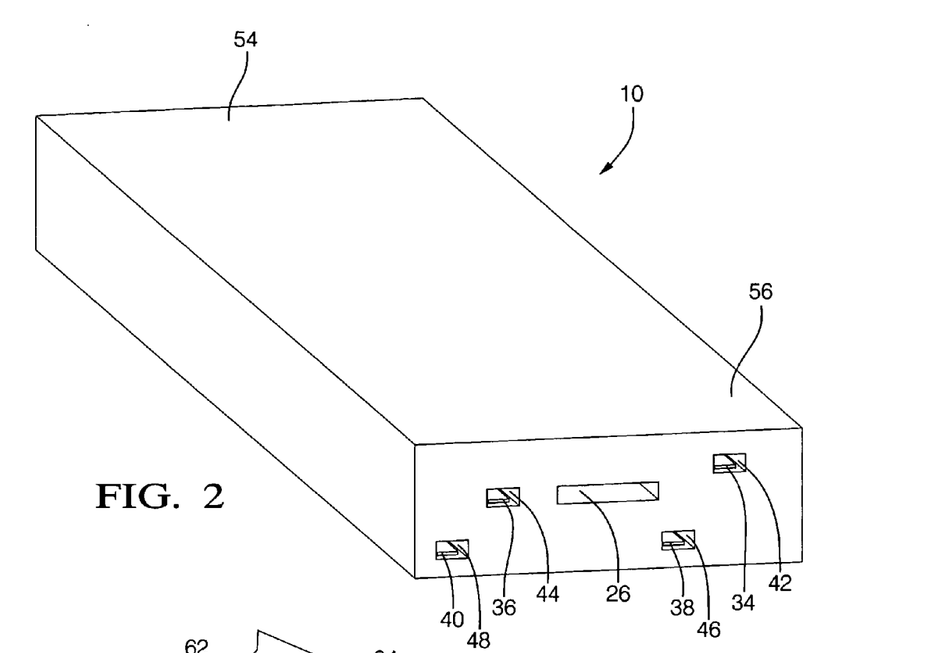
FIG. 2 is an end view of an exemplary embodiment of a gas sensor element.

As shown in FIGS. 1 and 2, the ceramic device (e.g., sensor element) 10 comprises a front-end portion 54 and a rear portion 56, wherein the front-end portion 54 comprises sensing elements (e.g., sensing electrode 12, electrolyte 16, and reference electrode 14) and the rear portion 56 comprises electrical connections (e.g., sockets (42, 44, 46, 48)). It is noted that the rear portion 56 can comprise any portion of the sensor element 10 comprising the leads. Furthermore, the term rear portion is used merely as a descriptive term to describe the end of the sensor element 10 opposite the sensing end of the sensor element 10. As such, the sockets may be disposed at a back end, and/or any side of the sensor element in a portion of the sensor element located away from the sensing end (i.e., the rear portion 56). Leads (34, 36, 38, 40), which supply potential to the heater element 28 and/or detect signal from the electrodes (12, 14), internally span the length of the sensor element 10 such that they are in electrical communication with the heater element 28 and/or the electrodes (12, 14) and extend within a socket (42, 44, 46, 48) at the rear portion 56. For example, lead 34 may be disposed on the same layer as the sensing electrode 12 where it is in electrical communication with the sensing electrode 12 near the front-end portion 54, and span the length of the sensor element 10 ending at the rear portion 56 within socket 42. As will be discussed in greater detail, the leads (34, 36, 38, 40) are in electrical communication with the heater element 28 and/or electrodes (12, 14) without the use of related vias and contact pads. As is illustrated in FIG. 1, the end of the sensor element 10 opposite the sensing end does not need vias with contact pads to establish electrical communication with the leads.

FIG. 2 illustrates a rear view of the sensor element 10, wherein the rear portion 56 is more clearly depicted. The exemplary sensor element 10 shown in FIG. 2 depicts sockets (42, 44, 46, 48), leads (34, 36, 38, 40), and reference gas channel 26. When a sensor element is formed, green tapes are typically stacked with leads disposed thereon. Sockets (e.g., 42, 44, 46, 48) may be created in the rear portion 56 by removing (e.g., punching out or otherwise removing), where desired, a portion of green tape. The opening is then maintained during firing of the sensor by at least partially filling the socket created thereby with a fugitive material (i.e., a material that burns away when the sensor element is fired), or by green stage forming with a tool, which may be withdrawn prior to firing. After the sensor element is fired, the final socket is formed, since the material surrounding the socket is densified, and any fugitive material has been removed.

The socket is positioned in the sensor 10 such that a lead spanning the interior length of the sensor element 10 (i.e., from an electrode or heater to the socket) continues within the socket such that a surface of the lead is exposed on an inside surface of the socket. It is understood by those skilled in the art that any number of configurations of sockets are possible. The number, size, shape, location, and configuration of the sockets may vary depending on the application. For example, if a second heater (not shown) were added to the sensor element 10, additional leads might be added, which in turn would relate to additional sockets. Desirably, the socket is at least partially (preferably wholly) in the same plane as the lead. The sockets (e.g., 42) are preferably disposed through the end 58 and/or an edge 60 at/near (hereinafter "near") the rear portion 56 of the sensor element 10. (See FIG. 3) Additionally, the socket(s) are preferably disposed on a plane parallel to a plane comprising the associated lead (e.g., see socket 40 and lead 34). The sockets are designed to receive a terminal element 50 that is preferably directly connected to a wire 52. In other words, the terminal element 50 inserts into the socket 42 such that it is in direct electrical communication with the lead 34 and the wire 52; contact pads are not needed to establish electrical communication between a wiring harness and the leads.

In contrast to the disclosed design, vias are metal filled extensions disposed perpendicular to the plane of the leads, extending from the sensing side 62 through the layers toward the heater side 64, and in electrical communication with a wiring harness through contact pads (disposed on an external surface of the sensor element at the rear portion) and connectors disposed at the end of the wires. Essentially, the electrically conductive metal fills the vias and contacts both the associated lead and the associated contact pad. The wiring harness connects to the contact pad to establish the desire communication.

The present design enables the wiring harness to connect directly to the lead, e.g., the terminal element on the wiring harness mates with the socket. For example, the terminal (e.g., the terminal element, which may be a single connector from the wires to the lead), disposed at the end of an appropriate wire, physically contacts both the lead and the wire. Additionally, depending upon the type of connection, the terminal element may be removably disposed in the socket; e.g., the terminal element can mate with the socket, wherein the socket is a chamber having a portion of a lead disposed into it. For example, in one embodiment, the terminal element could be disposed in a socket that extends through a side of the sensor element. The terminal element would physically contact the lead (e.g., that may be disposed at the end of the socket opposite the opening at the side of the sensor element) and physically contact a wire to establish communication between a control module and the electrode.

Figure 3:
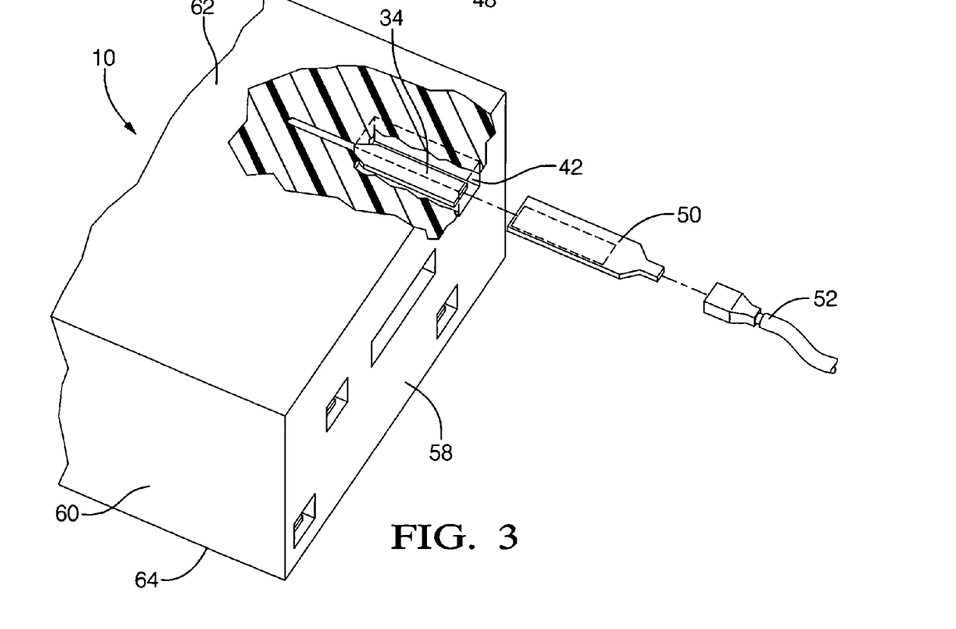
FIG. 3 is a partial prospective view of an exemplary embodiment of a gas sensor element.

FIG. 3 illustrates an exemplary embodiment, wherein socket 42 is mated with a terminal element 50. The terminal element 50 is inserted into the socket 42, such that the terminal element 50 is in electrical communication with lead 34 within the socket 42. The terminal element 50 (e.g., a pin, bar, rod, wire, spring terminal, or the like) may be joined to lead 34 within socket 42 by brazing, soldering, pressure contact, and the like, wherein an electrical and preferably a metallurgical, connection are made. Additionally, the terminal element may be joined to the unmetallized portion of the socket with an active metal braze or otherwise. The terminal element 50 may be coupled to a wire 52 (e.g., by crimping, welding, and the like), such that the terminal element is in electrical communication with the wire 52. The terminal element 50 establishes electrical communication between associated lead and a power source (not shown), e.g., the terminal element with associated wires (a wiring harness) can be connected to a control module that can receive the signals from the sensor. The use of a socket 42 and terminal element 50 enables the lead 34 to be in electrical communication with an external power source, meter, or the like (hereinafter referred to as "power source") without the use of vias (metal filled openings disposed laterally through the sensor) or contact pads. It is noted that terminal element 50 may be part of a plug (not shown).

Various materials can be employed for the terminal elements. Generally, it is preferable to match the coefficient of thermal expansion (CTE) of the terminal element and the sensor, with matching the terminal element CTE with the CTE of the portion of the sensor that may be contacted by the terminal element more preferred. Some possible terminal element materials include iron/nickel/cobalt alloy (e.g., KOVAR® (less than or equal to 0.2 wt. % C, 0.3 wt. % Mn 0.20 wt. % Si, 29.00 wt. % Ni, 17.00 wt. % Co, 53.3–53.5 wt. % Fe, wherein the weight percents are based on the total weight of the alloy), an iron/nickel alloy material, steels (e.g., 400 series stainless steels, and the like), and the like, as well as combinations comprising at least one of the foregoing materials.

With respect to the size and geometry of the terminal element(s), they preferably have a size and geometry that enables mating with the appropriate socket and that enables the maintenance of electrical communication between the terminal element and the lead.

Maintenance of the terminal element in electrical communication with the lead can be attain with appropriate terminal element design as well as with the use of adhesive, braze, welds, and the like (e.g., adhesion material(s)). Preferably, adhesion material(s) are chosen based upon various operating, manufacturing, and use factors such as compatibility of the materials (e.g., wettability, thermal expansion, ductility, and the like), process conditions (e.g., brazing process conditions such as vacuum, reducing gas, inert gas, temperature, time, and the like), and oxidation resistance at extreme service conditions, as well as other durability design parameters. For example, active metal and/or non-active metal braze types could be used to form the braze joint. Possible braze materials include various metals and alloys such as silver (Ag), nickel (Ni), vanadium (V), gold (Au), cobalt (Co), titanium (Ti), copper (Cu), and the like, as well as alloys and combinations comprising at least one of the foregoing metals. For example, the sensor can have a Fe/Ni/Co system (e.g., alloy, mixture, or the like) terminal element brazed into a platinum (Pt) pad metallized socket using one or more of the following braze materials: an active metal system (e.g., Ag/Cu/Ti system, Ti/Cu/Ni system, Au/Ni/V system, or the like) and/or a non-active metal systems (e.g., Ag/Cu system, or the like).

Disposed in electrical communication with the leads (e.g. 34, 36) are electrodes 12, 14. The sensing electrode 12, which is exposed to the exhaust gas during operation, preferably has a porosity sufficient to permit diffusion of gas molecules therethrough. Similarly, the reference electrode 14, which can be exposed to a reference gas such as oxygen, air, or the like, during operation, preferably has a porosity sufficient to permit diffusion of gas molecules therethrough. These electrodes can comprise a metal capable of ionizing oxygen, including, but not limited to, platinum, palladium, gold, osmium, rhodium, iridium and ruthenium; and metal oxides, such as zirconia, yttria, ceria, calcium oxide, aluminum oxide (alumina), and the like; as well as combinations comprising at least one of the foregoing metals and metal oxides. Other additives such as zirconia may be added to impart beneficial properties such as inhibiting sintering of the platinum to maintain porosity.

The electrodes 12, 14 are typically disposed on opposite sides of electrolyte 16 (although the present electrical connection method is applicable to applications where the electrodes are disposed on the same side of the electrolyte 16). The electrolyte 16, which may be a solid electrolyte, can be formed of a material that is capable of permitting the electrochemical transfer of oxygen ions while inhibiting the passage of the gas to be sensed (e.g., of the exhaust gases). Possible electrolyte materials include zirconium oxide (zirconia), cerium oxide (ceria), calcium oxide, yttrium oxide (yttria), lanthanum oxide, magnesium oxide, and the like, as well as combinations comprising at least one of the foregoing electrolyte materials, such as yttria doped zirconia, and the like.

A protective layer 18, optionally disposed on the side of the sensing electrode 12, opposite solid electrolyte 16, is designed to protect the sensing electrode from damage and poisoning while allowing the sensing electrode 12 to sense the particular gas without inhibiting the performance of the sensor element 10. Possible materials for the protective layer include spinel, alumina, (such as, delta alumina, gamma alumina, theta alumina, and the like) and the like, as well as a combination comprising at least one of the foregoing materials.

Heater element 28 can be employed to maintain the sensor element at the desired operating temperature. Heater element 28 can be a heater capable of maintaining a sensing end of the sensor element 10 adjacent the electrodes (12, 14) at a sufficient temperature to facilitate the various electrochemical reactions therein, with a preferred operating temperature of about 650° C. to about 800° C., and an operating temperature of about 700° C. to about 750° C. more preferred. Heater element 28, which can comprise, for example, platinum, tungsten, palladium, and the like, as well as a mixture, oxide, and alloy comprising at least one of the foregoing metals. The heater element 28 can be screen printed or otherwise disposed onto a substrate (e.g., insulating layers 30, 32), to a thickness of about 5 micrometers to about 50 micrometers, with about 10 micrometers to about 40 micrometers more preferred. Moreover, additional heaters (not shown) may be added to the sensor element 10 depending on the application.

Optional insulating layers 30, 32 provide structural integrity (e.g., protect various portions of the sensor element from abrasion and/or vibration, and the like, and provide physical strength to the sensor), and physically separate and electrically isolate various components. The insulating layer(s) can each have a thickness of greater than or equal to about 200 micrometers, with a thickness of about 50 micrometers to about 200 micrometers preferred. The insulating layers 30, 32 can comprise an aluminum oxide (alumina) or other dielectric material similar to those materials discussed above with regard to protective layer 18.

Leads (34, 36, 38, 40), which supply current to the heater element 28 and/or the electrodes (12, 14), are in electrical communication with the heater element 28, optional temperature sensor(s) (not shown) and/or the electrodes (12, 14). At the rear portion 56 of the sensor element 10, the leads continue within their respective sockets such that the leads may be disposed in electrical communication with a terminal element (e.g. 50). For example, a surface of each respective lead can cover a side of the socket, e.g., the lead within the socket can comprises a lateral dimension substantially equal to the lateral dimension of the socket. Furthermore, if the sensor element comprises a socket that is substantially rectangular in shape, the portion of the lead within socket may preferably have a substantially rectangular shape (e.g., see FIG. 3). The lead may optionally be disposed on a portion of the interior surface of the socket (e.g., along one wall if the socket is multisided; and along a portion of the socket if it is round), may have about the same length as the socket, and may be smaller in area than the side of the socket on which it is disposed (e.g., the nominal inside face of a rectangular prismatic socket). In other words, the length and/or width of the portion of the lead in the socket may or may not be equivalent to the length and/or width of the side of the socket in which the lead is disposed so long as a sufficient amount of lead is disposed in the socket to enable electrical communication between the lead and the terminal element. For manufacturing, cost, and assembly purposes, the portion of the lead disposed in the socket preferably does not have the same shape as the socket. In other words, the portion of the lead within the socket may, for example, be wider compared to the portion of the lead that is not within the socket. The leads (34, 36, 38, 40) may comprise an electrically conductive metal, such as platinum, palladium, gold, ruthenium, tungsten, and the like, as well as oxides, alloys, and mixtures comprising at least one of the foregoing.

Sockets (42, 44, 46, 48) are positioned within the sensor element 10 such that they engage at least a portion of the leads (34, 36, 38, 40) at appoint distal from the sensing end 54. Although the socket can have any shape or configuration, the socket preferably comprises a shape that allows for ease in mating with the terminal element 50. For example, as depicted in FIG. 3, the socket 42 may comprise a substantially rectangular shape, wherein the lead 34 is disposed on a surface of the substantially rectangular socket. The substantially rectangular shape of the socket 42 relates to the substantially rectangular shape of the terminal element 50 resulting in ease in mating.

Terminal element 50 may be connected to a wire 52 (e.g., by crimping, welding, and/or the like), wherein the terminal element 50 is in electrical communication with the wire 52, which may be in electrical communication with a power source or meter (not shown). The terminal element 50 disposed in electrical communication with the appropriate lead in any fashion that enables, and preferably maintains, electrical communication therebetween, such as by brazing, soldering, clipping, and the like, wherein an electrical connection between the terminal element and the lead is made, and metallurgical connection is preferably made.

The number of terminal elements relates to the number of sockets, and may vary depending on the application. Although the terminal element can have any shape that enables electrical communication with the lead, it preferably comprises a shape that allows for ease in mating with the socket. The terminal element comprises an electrically conductive metal, for example, 400 series stainless steel, nickel, nichrome, alloy 42 (about 42 wt. % Ni and about 58 wt. % Fe, wherein weight percent is based on total weight percent of alloy), KOVAR®, and the like preferred. The terminal element may further comprise a second conductive metal that is plated, embedded, coated, butt-joined, skarfjoined, and/or the like, on/within the first conductive metal. For example, this second conductive metal may be a braze, solder, or the like. Also, the braze may be applied to the terminal element in paste form, by dipping or brushing, prior to insertion into the socket.

In a method of making a planar sensor element, the sensor element components, e.g., electrodes 12, 14, electrolyte 16, insulating layer(s) 30, 32, heater element 28, protective layers 18 and the like, are formed using techniques such as tape casting methods, sputtering, punching and placing, spraying (e.g., electrostatically spraying, slurry spraying, plasma spraying, and the like), dipping, painting, screen printing, and the like, as well as combinations comprising at least one of the foregoing techniques. The electrolyte 16 may be formed and fired, and the electrodes 12, 14 formed subsequently. Alternatively, the electrolyte 16 and one or both of the electrodes 12, 14 may be formed, and the electrolyte 16 and electrode 12 and/or 14 as well as additional layers co-fired. Leads (34, 36, 38, 40) may be placed on the same layers as electrodes 12, 14 and/or heater element 28 before the sensor element is fired. Once the leads are placed, prior to firing, the relating sockets (42, 44, 46, 48) are formed, wherein a lead within a given socket is preferably disposed adjacent to one inside surface of the socket to enable facile mating with the terminal element. The sockets can be formed, for example, by punching out the necessary tape layers, filling the socket with fugitive material or placing a tool into the socket. In other embodiments, the sockets can be displaced with a tool when the layers are pressed together. After laminating the layers, if the sockets were made with a tool, the tool is removed, and the elements are then fired. The sockets may be optionally filled with a fugitive material. The firing temperature is dependent upon the type of sensor and the materials to be fired. Generally the temperature is about 800° C. to about 1,500° C.

For placement in a gas stream, sensor element 10 may be disposed within a protective casing (not shown) having holes, slits or apertures, generally to limit the overall exhaust gas flow contacting sensor element 10. This arrangement extends the useful life of sensor element 10 by minimizing the ion transport through the electrodes and electrolyte. It also reduces abrasion damage and generally protects from contaminants in the exhaust gas stream.

In operation, the sensor is positioned to expose the sensing element (e.g. 10) to the gas to be sensed. When the sensor (i.e., the sensor element disposed within the casing)

is exposed to an exhaust gas, for example, oxygen that has not been consumed during combustion enters the sensor through the protective coating 24, protective layer 18 where it can be sensed by sensing electrode 12 due to a potential difference between sensing electrode 12 and reference electrode 14.

Advantageously, a gas sensor with sockets that enable electrical communication to the leads offers a number of improvements over sensor elements that have vias or contact pads. For example, the use of sockets and terminal elements may enable an element geometry change, wherein more elements can be yielded per tile. Further, eliminating or reducing the number of vias and contact pads may reduce the amount of precious metal used in the sensor element, since vias and contact pads generally comprise a precious metal (e.g., platinum). Additional cost savings result by eliminating process steps associated with via use, e.g., via punch and via fill steps.

Unlike vias that are disposed laterally through the rear of the sensor element (i.e., across the plane of the sensor layers and the leads) creating electrical communication between leads and contact pads disposed on the outer surface of the sensor at the rear, the sockets can be disposed into the rear portion 56 of the sensor (e.g., either at the end or on the side). Whereas the vias were disposed through the many layers of the sensor, i.e., perpendicular to both the major axis of the sensor and the plane of the layers and the lead, the sockets are disposed parallel to the plane of the layers, and preferably parallel to the major axis of the sensor. Optionally, the terminal connections can be completely encased within the sensor if the sockets have sufficient depth. Such encasement is believed to improve electrical isolation resistance because contaminants that may collect on the surface of the sensor may not decrease the isolation resistance between terminals. Essentially, clamshell-type contact pad connection systems apply a clamping load to the sensor during the packaging process. The encased connections, however, relax the need for such a high degree of element flatness, as no clamping load is applied to the element. Further, the terminal elements simplify connection design possibilities, for example, a connector body with socket openings can be mated directly to brazed terminal elements.

Preferably, each socket receives an end of a lead and a terminal element such that the terminal element is disposed in electrical communication with the lead, and on a parallel plane as the layers of the sensor (see FIG. 3). The terminal element can be a single element or can be in the form of a plug comprising a plurality of terminal elements designed to plug into the rear portion of the sensor. The use of terminal element(s) and socket(s) eliminates the need for contact pads.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A sensor, comprising:
   a sensing element formed of a plurality of ceramic layers arranged and fired to form a planar structure having an end, said sensing element further comprising an electrolyte and first and second electrodes in ionic communication with the electrolyte; said sensing element comprising
   a first socket extending from said end and defining a first chamber configured to receive a first terminal element;
   a first lead disposed in electrical communication with the first electrode and having a surface exposed within said first socket for contact with the first terminal element;
   a second socket extending from said end and defining a second chamber configured to receive a second terminal element; and
   a second lead disposed in electrical communication with the second electrode and having a surface exposed within said second socket for contact with the second terminal element.

2. The sensor of claim 1, further comprising the first terminal element disposed in the first socket and in electrical communication with the first lead.

3. The sensor of claim 1, further comprising
   a first heater socket extending from said end and defining a first heater chamber configured to receive a first heater terminal element; and
   a first heater lead disposed in electrical communication with a heater element and having a surface exposed within said first heater socket for contact with the first heater terminal element.

4. The sensor of claim 1, further comprising a plug comprising the first terminal element and the second terminal element, wherein the first terminal element is disposed in the first socket in physical contact and electrical communication with the first lead, and the second terminal element is disposed in the second socket in physical contact and electrical communication with the second lead.

5. The sensor of claim 4, further comprising a first braze disposed between the first terminal element and at least one of the first socket and the first lead.

6. The sensor of claim 1, wherein the sensor is selected from the group consisting of planar gas sensor, field effect transistor, semiconductor, and resistance temperature detector.

7. The sensor of claim 1, further comprising a wiring harness physically connected to the sensor element and configured for electrical communication with a control module, wherein the wiring comprises
   the first terminal element disposed in the first socket and in physical contact and electrical communication with the first lead and with a first wire; and
   the second terminal element disposed in the second socket and in physical contact and electrical communication with the second lead and with a second wire.

8. The sensor of claim 7, wherein the wiring harness is removably connected to the sensor element.

9. A sensor, comprising:
   a wiring harness configured for electrical communication with a control module and comprising a first terminal element in electrical communication with a first wire, a second terminal element in electrical communication with a second wire, first heater terminal element in electrical communication with a first heater wire, and second heater terminal element in electrical communication with a second heater wire;

a sensor element comprising a plurality of planar layers formed of a ceramic material and having an end, said sensor element further comprising a first electrode and a second electrode in mutual ionic communication with an electrolyte;

a heater element in thermal communication with the first electrode and the second electrode;

a first socket extending from the end and defining a first chamber configured to receive the first terminal element;

a first lead disposed in electrical communication with the first electrode and having a surface exposed within the first socket;

a second socket extending from the end and defining a second chamber configured to receive the second terminal element;

a second lead disposed in electrical communication with the second electrode and having a surface exposed within the second socket;

a first heater socket extending from the end and defining a first heater chamber configured to receive the first heater terminal element;

a first heater lead disposed in electrical communication with the heater element having a surface exposed within the first heater socket;

a second heater socket extending from the end and defining a second chamber configured to receive the second heater terminal element; and a second heater lead disposed in electrical communication with the heater element having a surface exposed within the second heater socket;

wherein the first terminal element is in electrical communication with the first lead, the second terminal element is in electrical communication with the second lead, the first heater terminal element is in electrical communication with the first heater lead, and the second heater terminal element is in electrical communication with the second heater lead.

10. A method for making a sensor, comprising:

arranging a plurality of ceramic layers to from a planar structure having an end, said planar structure further comprising an electrolyte, a first electrode and a second electrode in contact with the electrolyte first lead disposed from the first electrode to said end and a second lead from the second electrode to said end;

forming a first socket extending from the end and defining a first chamber configured to receive a first terminal element, wherein the first lead is exposed within the first socket;

forming a second socket extending from the end and defining a second chamber configured to receive a second terminal element, wherein the second lead is exposed within the second socket; and firing the planar structure to form the sensor element such that the first socket defines a first chamber configured to receive a first terminal element and the second socket defines a second chamber configured to receive a second terminal element.

11. The method of claim 10, further comprising disposing a first terminal element in the first socket such that the first terminal element is in electrical communication with the first lead.

12. The method of claim 11, wherein the first terminal element is metallurgically connected to the first lead.

13. The method of claim 11, wherein the first terminal element is mechanically connected to the first lead.

14. The method of claim 10, further comprising disposing a second terminal element in the second socket such that the second terminal element is in electrical communication with the second lead.

15. The method of claim 10, wherein forming the first socket further comprises forming a first opening into the sensing element and disposing first fugitive material in the first opening, and wherein forming the second socket further comprises forming a second opening into the sensing element and disposing second fugitive material in the second opening.

16. The method of claim 10, wherein forming the first socket further comprises disposing a first tool into and/or between a first layer of the sensor element.

17. A method for sensing a gas, comprising:

contacting a sensor element with a gas to be sensed, wherein the sensor element comprises a first electrode and a second electrode in mutual ionic communication with an electrolyte;

a first socket defining a first chamber configured to receive a first terminal element;

the first terminal element disposed in the first socket and in physical and electrical communication with a first wire;

a first lead disposed in electrical communication with the first electrode and in physical and electrical communication with the first terminal element;

a second socket defining a second chamber configured to receive a second terminal element;

the second terminal element disposed in the second socket and in physical and electrical communication with a second wire;

a second lead disposed in electrical communication with the second electrode and in physical and electrical communication with the second terminal element;

wherein the first terminal element and the second terminal element are in electrical communication with a control module; and producing an electromotive force.

18. A ceramic device, comprising:

a first lead and a second lead are disposed within a ceramic element, a first socket is disposed near a rear portion of the ceramic element and defining a first chamber for receiving a first terminal element, wherein the first lead is disposed in physical communication with and extends into the first socket, and the first socket is disposed on a first socket plane that is parallel a first lead plane comprising the first lead;

the first terminal element is disposed in the first socket and electrical communication with the first lead;

a second socket is disposed near a rear portion of the ceramic element and defining a second chamber for receiving a second terminal element, and wherein the second lead is disposed in physical communication with and extends into the second socket, and the second socket is disposed on a second socket plane that is parallel a second lead plane comprising the second lead;

the second terminal element is disposed in the second socket and in electrical communication with the second lead;

a first resistor lead and a second resistor lead are disposed on a resistor plane within the ceramic element;

a first resistor socket is disposed in a rear portion of the ceramic element and defining a first resistor chamber for receiving a first resistor terminal element, wherein the first resistor lead is disposed in physical communication with and extends into the first resistor socket;

a second resistor socket is disposed in a rear portion of the ceramic element and defining a second resistor chamber for receiving a second resistor terminal element wherein the second resistor lead is disposed in physical communication with and extends into the second resistor socket; and wherein the first resistor socket and the second resistor socket are disposed on a resistor socket plane that is parallel to the resistor plane;

a first resistor terminal element is disposed in the first resistor socket and in electrical communication with the first resistor lead; and a second resistor terminal element is disposed in the second resistor socket and in electrical communication with the second resistor lead.

* * * * *